United States Patent [19]
Gurtler et al.

[11] Patent Number: 5,773,021
[45] Date of Patent: Jun. 30, 1998

[54] BIOADHESIVE OPHTHALMIC INSERT

[75] Inventors: Florian Gurtler, Chene Bougeries; Robert Gurny, Geneva, both of Switzerland

[73] Assignee: Vetoquinol S.A., Lure, France

[21] Appl. No.: 751,561

[22] Filed: Nov. 18, 1996

Related U.S. Application Data

[63] Continuation of Ser. No. 209,913, Mar. 14, 1994, abandoned.

[51] Int. Cl.$^6$ ........................................... A61F 2/00
[52] U.S. Cl. ................................................ 424/427
[58] Field of Search ............................................. 424/427

[56] References Cited

U.S. PATENT DOCUMENTS

| | | | |
|---|---|---|---|
| 3,870,791 | 3/1975 | Haddad et al. | 424/22 |
| 4,014,335 | 3/1977 | Arnold | 128/260 |
| 4,160,020 | 7/1979 | Ayer et al. | 424/15 |
| 4,179,497 | 12/1979 | Cohen et al. | 424/22 |
| 4,186,184 | 1/1980 | Zaffaroni | 424/14 |
| 4,343,787 | 8/1982 | Katz | 424/78 |
| 4,709,996 | 12/1987 | Michelson | 350/418 |
| 5,137,728 | 8/1992 | Bawa | 424/427 |
| 5,164,188 | 11/1992 | Wong | 424/428 |
| 5,188,826 | 2/1993 | Chandrasekaran | 424/78.04 |
| 5,192,535 | 3/1993 | Davis et al. | 424/78.04 |
| 5,225,196 | 7/1993 | Robinson | 424/427 |
| 5,318,780 | 6/1994 | Viegas et al. | 424/427 |
| 5,340,572 | 8/1994 | Patel et al. | 424/427 |

FOREIGN PATENT DOCUMENTS

| | | |
|---|---|---|
| 0 077 261 | 4/1983 | European Pat. Off. . |
| 0 246 653 | 11/1987 | European Pat. Off. . |
| 0 316 838 | 5/1989 | European Pat. Off. . |
| 2 305 173 | 10/1976 | France . |
| 2 319 375 | 2/1977 | France . |
| 62-229250 | 9/1987 | Japan . |

OTHER PUBLICATIONS

"Bioadhesive Ophthalmic Drug Inserts (BODI) Containing Gentamicin", F. Gurtler et. al., Fifth European Congress of Biopharmaceutics and Pharmacokinetics, Apr. 20–22, 1993.

*Primary Examiner*—Helen L. Pezzuto
*Attorney, Agent, or Firm*—Finnegan, Henderson Farabow, Garrett & Dunner, L.L.P.

[57] ABSTRACT

A bioadhesive ophthalmic insert is described which is intended more particularly for the prolonged and controlled release of a medicinal substance. The insert comprises a composite polymeric material matrix in which the medicinal substance is incorporated.

The composite polymeric material matrix comprises a water-soluble biocompatible polymer and a bioadhesive biocompatible polymer and, where applicable, a water-insoluble biocompatible polymer.

11 Claims, No Drawings

BIOADHESIVE OPHTHALMIC INSERT

This is a continuation of application Ser. No. 08/209,913, filed Mar. 14, 1994, now abandoned.

The invention relates to a bioadhesive ophthalmic insert, more particularly a bioadhesive ophthalmic insert intended for the prolonged and controlled release of one or more medicinal substances.

BACKGROUND

Numerous pharmaceutical compositions have hitherto been known in both human and veterinary medicine for use in the treatment of the most widely varying eye disorders, e.g., inflammation, such as conjunctivitis, viral or bacterial infections, glaucoma or dry eye syndrome. These compositions are most usually in the form of eye lotions, gels, ointments, films, or inserts which, in the latter case, are placed either in the conjunctival sac or beneath the top eyelid.

Ophthalmic inserts are used more particularly when the prescribed treatment is to be of a long duration or requires an extended contact time of the active principle or alternatively when the applications have to be repeated frequently. In such cases, the comfort of the patient is also a requisite, and is allowed for by reducing the number of operations required, for example, and the same applies to controlled release of the active substance over a sufficiently long period. Inserts of this kind have mainly been produced from a water-soluble polymer or copolymer, inter alia from a water-soluble cellulose derivative incorporating the active substance in varying proportions (for example see U.S. Pat. Nos. 4,179,497, 4,343,787, 3,870,791 or EP-A-0 108 661). A single polymeric material is then used, and the attempt is made to adapt it to the required objective depending on its actual characteristics, by varying parameters such as viscosity, molecular weight, and crystallinity, for example. However, the available room for manoeuvre is very much limited.

At the present time, the ophthalmic inserts available do not provide prolonged residence times with a guarantee of suitable release of the active substance. Also, accidental movement of the insert is frequently observed, the insert passing either behind the eye or leaving the socket. The invention has the advantage of proposing a new type of ophthalmic insert which advantageously enables such disadvantages to be obviated, while inter alia ensuring permanent positioning and lasting release of the active medicinal principle.

SUMMARY OF THE INVENTION

The invention relates to a bioadhesive ophthalmic insert, more particularly a bioadhesive ophthalmic insert intended for the prolonged and controlled release of at least one medicinal substance, comprising a matrix of composite polymeric material in which the medicinal substance is incorporated, the said polymeric composite material matrix comprising:

a water-soluble biocompatible polymer and a bioadhesive biocompatible polymer.

The invention also relates to an ophthalmic insert as defined above characterised by a matrix of composite polymeric material comprising:

a water-insoluble biocompatible polymer, a water-soluble biocompatible polymer and a bioadhesive biocompatible polymer.

DESCRIPTIONS OF PREFERRED EMBODIMENTS

Advantageously, the composite polymeric material matrix of the insert according to the invention comprises from 50 to 99.5% by weight of the water-soluble biocompatible polymer and from 0.5 to 5.0% by weight of the bioadhesive biocompatible polymer, any remainder up to 100% by weight being provided by the water-insoluble biocompatible polymer.

According to the invention, the water-soluble biocompatible polymer used is advantageously a hydroxyalkyl cellulose, a maltodextrin, a chitosan, a modified starch, such as, for example, a pregelatinised starch, a destructured starch (see for example U.S. Pat. No. 4,900,361) or a partially hydrolysed starch, or alternatively a polyvinyl alcohol, this list being in no way exhaustive. Preferably, a hydroxyalkyl cellulose is used, such as a hydroxyethyl cellulose or a hydroxy-propyl cellulose of a molecular weight between 10,000 and 1,000,000 or more, preferably between 80,000 and 125,000. Products of this kind are available in the specialised trade.

According to the invention, the water-insoluble biocompatible polymer used is advantageously a water-insoluble alkyl cellulose, preferably an ethyl cellulose, for example EC-N 50 NF® (Hercules) or Ethocel® (Premium Dow). Added in adequate proportions to the mass of water-soluble polymer, the effect of the ethyl cellulose is to prolong substantially the dissolution time of the ophthalmic insert and hence the period of release of the medicinal substance. Surprisingly, the incorporation of ethyl cellulose in the polymeric material selected according to the invention results in complete dissolution of the insert nevertheless.

According to the invention, the polymeric material matrix comprises a bioadhesive polymer, i.e. a natural or synthetic polymer capable of stable interaction with a biological substrate, such as the mucosa of the conjunctival sac, for example. The bioadhesive biocompatible polymer used is advantageously a polymer of the polyvinyl carboxylic acid type (carboxy vinylpolymer) or alternatively certain bioadhesive polysaccharides or polysaccharide derivatives, such as, for example, cellulose ethers, methylhydroxyethyl cellulose (Benecel® ME Aqualon, Tylose® MH Hoechst) or methylhydroxypropyl cellulose (Benecel® MP Aqualon), for example. It is also possible to use sodium carboxymethyl celluloses, such as Blanose® Type 7 or 9 (Aqualon) or Tylose® C (Hoechst) for example.

Preferably, a non-neutralised polyvinyl carboxylic acid is used of a molecular weight between 450,000 and 4,000,000, such as a Carbopol® 934 P, 980, 984, 954, (Goodrich) or Noveon® AA1 (Goodrich). This use of non-neutralised material in an ophthalmic insert is at first sight surprising since it is recognised as an irritant. In actual fact, it is normally used in the form of a sodium salt. Dispersed in adequate proportions within the mass of polymeric material this type of bioadhesive polymer loses its irritant character and guarantees a prolonged residence time for the insert. Also, this type of polymer ensures positioning of the insert in its initial position, thus offering all the required security.

According to the invention, the polymers listed above are also selected in dependence on their extrudable or thermoformable character, the guarantee of an optimal preparation process, more particularly insofar as concerns intimate mixing of the constituents and incorporation of the medicinal substance. Mixing of the selected ingredients and their subsequent extrusion or thermoforming may be effected by means of the conventional techniques.

In one preferred embodiment of the invention, the constituents of the composite polymeric material matrix are divided up as follows:

hydroxypropyl cellulose 50 to 99.5% by weight non-neutralised polyvinyl carboxylic acid 0.5 to 5.0% by weight, any remainder up to 100% by weight being ethyl cellulose.

According to the invention, 0.5 to 50% by weight, for example about 25% by weight, of medicinal substance is generally incorporated in the insert depending on the nature of the medicinal substance, the type of disorder to be treated and the required effect. The insert according to the invention will more generally be in the form of a small rod, disc, pastille or film, depending on requirements.

As an example of medicinal substance, the most diverse appropriate agents can be used, such as antibacterial, antiviral, antimycotic, anti-glaucoma, antiphlogistic, anti-inflammatory, anti-allergy, vasoconstrictive, vasodilatory, myotic, mydriatic, or anaesthetic agents or alternatively lubricating action preparations (artificial tears). However, this list is not exhaustive.

The medicinal substance will be advantageously submitted before its incorporation in the composite polymeric material matrix, to a physical pretreatment for decreasing its release rate.

This physical pretreatment may for example consist in changing the medical substance into an inclusion product in a support (form such as liposomes, coacervates, nanospheres or nanoparticles for example), into an adsorption product on a support or into a co-precipitation product with a support, said support being a pharmaceutically acceptable product which is water-soluble and/or biodegradable and/or able to lose its physical cohesion when brought into contact with a biological fluid.

However, according to a preferred embodiment, said physical pretreatment comprises forming a solid solution between said medicinal substance and a pharmaceutically acceptable product which is water-soluble and/or biodegradable and/or able to lose its physical cohesion when brought into contact with a biological fluid; the weight ratio of said medicinal substance to said product may vary in a broad range, a preferred range being 10/2 to 10/10.

The above mentioned support and product may for example be chosen among the acrylic acid polymers (PAA); methacrylic acid copolymers (such as EUDRAGIT® L or S); carboxylic acid esters of cellulose or cellulose derivatives such as cellulose acetate (CA), cellulose acetate phthalate (CAP), cellulose acetate trimellitate (CAT), cellulose acetate butyrate (CAB), cellulose acetate propionate (CAPr), hydroxypropylmethyl cellulose phthalate (HPMCP), hydroxypropylmethyl cellulose acetate succinate (HPMCAS), methylcellulose acid phthalate and ethyl (hydroxyethyl) cellulose acid phthalate; polymers of vinyl esters of carboxylic acids such as polyvinyl acetate phthalate (PVAP); carboxylic acid esters of starch such as starch acetate phthalate; and their mixtures.

The formation of said solid solution may be carried out by dissolving said pharmaceutically acceptable product which is water-soluble and/or biodegradable and/or able to lose its physical cohesion, in an appropriate solvent, adding under stirring the medicinal substance to the thus obtained solution, removing said solvent preferably by vacuum evaporation and crushing the solid residue.

The invention will be illustrated by reference to the following examples, which have no limiting force.

EXAMPLE 1

An insert was prepared which contained gentamycin sulphate as medicinal substance, incorporated in a proportion of 25% by weight in a binary polymeric material matrix produced from the following components:

hydroxypropyl cellulose (Klucel® HXF—Aqualon)

non-neutralised polyvinyl carboxylic acid (Carbopol® 934 P—Goodrich), to which was also added about 0.5% (with respect to the total weight) of sodium fluorescein as UV tracer.

The samples were prepared after intimate mixture of the above ingredients in powder form, followed by extrusion by means of a piston extruder, under the following conditions: extrusion temperature about 160° C., duration 2 minutes, extrusion pressure 200 kPa, die diameter 1.5 mm. To obtain perfect homogenisation of the various constituents, two successive extrusions were carried out. The inserts kept for experimentation were in the form of small rods 5 mm long and 1.35 to 1.45 mm in diameter.

For in vivo experimentation, the samples were deposited in the rear part of the conjunctival sac of rabbits (1 to 5 subjects per experiment). The presence or absence of the insert was then determined by means of an ultraviolet lamp, visual checks being made at regular intervals. The results obtained were combined in the following table:

| Sample No | HPC* % | Carbopol® % | Duration h | Rejection rate ** |
|---|---|---|---|---|
| 011 | 100 | 0 | 7 | 40 |
| 013 | 99.5 | 0.5 | 8 | 0 |
| 018 | 99.0 | 1.0 | 16 | 0 |

*hydroxypropyl cellulose
**number of inserts rejected expressed as a percentage

EXAMPLE 2

An insert was prepared which contained gentamycin sulphate as medicinal substance, incorporated in a proportion of 25% by weight in a ternary polymeric material matrix produced from the following components:

ethyl cellulose EC N-50 NF® hydroxypropyl cellulose (Klucel® HXF—Aqualon)

non-neutralised polyvinyl carboxylic acid (Carbopol® 934 P—Goodrich), to which there was also added about 0.5% (with respect to the total weight) of sodium fluorescein as ultraviolet tracer.

The samples were then subjected to the extrusion process described hereinbefore, and were then tested in vivo under identical conditions on rabbits. The results were collected in the following table:

| Sample No. | HPC* % | EC** % | Carbopol® % | Duration h | Rejection rate *** |
|---|---|---|---|---|---|
| 017 | 89.5 | 10.0 | 0.5 | 9 | 15 |
| 020 | 89.0 | 10.0 | 1.0 | 21 | 0 |
| 022 | 79.0 | 20.0 | 1.0 | 19 | 0 |
| 026 | 78.0 | 20.0 | 2.0 | 19 | 0 |
| 028 | 77.0 | 20.0 | 3.0 | 20 | 0 |
| 030 | 76.0 | 20.0 | 4.0 | 20 | 0 |
| 031 | 75.5 | 20.0 | 4.5 | 19 | 0 |

*Hydroxypropyl cellulose
**Ethyl cellulose
***number of inserts rejected expressed as a percentage

EXAMPLE 3

Preparation of inserts containing a solid solution of gentamicine-CAP and evaluation in dogs This preparation is carried out in three steps, i.e. preparation of the solid solution (I), preparation of the product to be extruded (II) and extrusion (III).

(I) Preparation of the solid solution Gentamicine-CAP

Dissolution, at reflux, of 90 g of CAP in 500 ml of acetone,

Addition, under stirring, of 150 g of Gentamicine sulphate,

Removing of the acetone by vacuum evaporation and then in a vacuum drying oven,

Crushing of the solid residue,

Sieving of the crushed residue for recovering particles having 500 μm (II) Preparation of the product to be extruded Mixing in a mixer HPC, EC and Carbopol® 934 P in the following proportions: HPC: 67%; EC: 30%; Carbopol® 934 P: 3%, Incorporation of 20 g of the solid solution prepared in step (I), to 30 g of the above-obtained mixture, Homogenization.

(III) Extrusion

Use is made of a BETOL® 1820J type laboratory screw extrusion device working under the following conditions: temperature of zone 1: 140° C.; temperature of zones 2 and 3: 150° C.; die diameter: 2 mm; extrusion temperature: 160° C.

This device is supplied with the preparation obtained in step (II),

Extrusion with a screw rotation speed of 20 to 40 rpm,

Evaluation of the Gentamicine concentration in dogs (Beagle).

The release of Gentamicine from the above-prepared inserts has been evaluated as follows:

The insert is deposited in the conjunctival sac, 4 μl of tears are taken as a sample at regular intervals and the Gentamicine concentration is determined by immunofluorescence polarization.

The results obtained are given in the following table (6 or 12 test animals per group).

TABLE

| Time (h) | 6 | 12 | 18 | 24 | 30 | 36 |
|---|---|---|---|---|---|---|
| Average [μg/ml] | 3767 | 3707 | 3519 | 3433 | 3357 | 3341 |
| Standard-Deviation [μg/ml] | 395 | 245 | 101 | 59 | 126 | 300 |
| Time (h) | 42 | 48 | 54 | 60 | 66 | 72 |
| Average [μg/ml] | 3320 | 3339 | 2671 | 1809 | 1108 | 462 |
| Standard-Deviation [μg/ml] | 142 | 194 | 85 | 111 | 39 | 10 |

The above results show that Gentamicine is present in an effective concentration, higher than the minimum inhibitive concentration during 72 hours.

EXAMPLE 4

Preparation of inserts by heat compression

Ophthalmic inserts of square section are prepared as follows:

After mixing of HPC (KLUCEL® HXF NF, Aqualon®), EC (EC N-50 NF® Hercules) and a derivative of polyacrylic acid (Carbopol® 934 P, Goodrich) in the following proportions: HPC: 80%; EC: 18% and Carbopol®: 2%), the obtained powder mixture is placed on the lower die of a heat compression concentration device. The heat compression is carried out with the following conditions: compression at $40.10^5$ Pa during one minute; temperature-rising: up to 150° C. and stalilization at this temperature during 1 mn; cooling by a pneumatic system up to room temperature; decreasing of the pressure and removal from the mold. The thus obtained product is cut to obtain extruded pieces having a length of 5 mm long and a square section of 1,5 mm width.

We claim:

1. An ophthalmic insert useful for the prolonged and controlled release of at least one medicinal substance, which comprises a homogeneous mixture of a composite polymeric material matrix and the medicinal substance, said composite polymeric material matrix comprising a mixture of:
    a water-soluble biocompatible polymer selected from hydroxyalkyl celluloses, maltodextrins, chitosans, modified starches or polyvinyl alcohols,
    a water-insoluble biocompatible polymer selected from alkylcelluloses, and
    a bioadhesive biocompatible polymer selected from polyvinyl carboxylic acids or sodium carboxymethyl celluloses,
    said insert being prepared by extrusion, thermoforming or heat compression of said homogeneous mixture.

2. An ophthalmic insert according to claim 1, wherein the composite polymeric material matrix comprises from 50 to 99.5% by weight of the water-soluble biocompatible polymer and from 0.5 to 5% by weight of the bioadhesive biocompatible polymer, any remainder up to 100% by weight being the water-insoluble biocompatible polymer.

3. An ophthalmic insert according to claim 1, wherein the hydroxyalkyl cellulose is a hydroxypropyl cellulose having a molecular weight of between 10,000 and 1,000,000.

4. An ophthalmic insert according to claim 1, which comprises 0.5 to 50% by weight of the medicinal substance.

5. An ophthalmic insert according to claim 1, wherein the medicinal substance is selected from the group consisting of antibacterial, antiviral, antimycotic, anti-glaucoma, antiphlogistic, anti-inflammatory, anti-allergy, vasoconstrictive, vaso-dilatory, myotic, mydriatic, anaesthetic and lubricant agents.

6. An ophthalmic insert according to claim 1, wherein the medicinal substance is in the form of an inclusion product in a support, an adsorption product on a support or a co-precipitation product with a support, said support being a pharmaceutically acceptable product which is at least one of water-soluble, biodegradable, and able to lose its physical cohesion when brought into contact with a biological fluid.

7. An ophthalmic insert according to claim 1, wherein the medicinal substance is in the form of a solid solution with a pharmaceutically acceptable product which is at least one of water-soluble, biodegradable, and able to lose its physical cohesion when brought into contact with a biological fluid.

8. An ophthalmic insert according to claim 7, wherein said pharmaceutically acceptable product is selected from the group consisting of acrylic acid polymers; methacrylic acid copolymers; carboxylic acid esters of cellulose or cellulose derivatives; polymers of vinyl esters of carboxylic acids; carboxylic acid esters of starch; and their mixtures.

9. An ophthalmic insert according to claim 1, wherein the bioadhesive biocompatible polymer is a non-neutralized polyvinyl carboxylic acid having a molecular weight of between 450,000 and 4,000,000.

10. A process for manufacturing an ophthalmic insert useful for the prolonged and controlled release of at least one medicinal substance, which comprises a matrix of a composite polymeric material in which the medicinal substance is incorporated, comprising forming a homogeneous mixture of:

a water-soluble biocompatible polymer selected from hydroxyalkyl celluloses, maltodextrins, chitosans, modified starches or polyvinyl alcohols, a water-insoluble biocompatible polymer selected from alkylcelluloses, a bioadhesive biocompatible polymer selected from polyvinyl carboxylic acids or sodium carboxymethyl celluloses, and a medicinal substance, and extruding, thermoforming or heat compressing said polymeric mixture.

11. A product produced by the process of claim 10.

* * * * *